United States Patent [19]

Shattock

[11] 4,198,211
[45] Apr. 15, 1980

[54] MICROBIOLOGICAL PROCESSES TO PRODUCE FUEL GAS

[76] Inventor: Geoffrey F. Shattock, 5 Orchard Close, Long La., Tielhurs, Reading Berkshire, England

[21] Appl. No.: 866,507

[22] Filed: Jan. 3, 1978

[30] Foreign Application Priority Data

Jan. 7, 1977 [GB] United Kingdom .................. 641/77

[51] Int. Cl.² ............................ C10J 1/06; C02C 1/14
[52] U.S. Cl. ............................. 48/197 A; 48/197 R;
71/8; 71/12; 165/163; 435/167; 210/12; 210/16
[58] Field of Search ................... 48/197 A, 111, 209,
48/197 R; 195/27, 33, 104; 210/12, 15, 16, 182,
187, 17; 71/8, 9, 10, 15, 12; 165/163

[56] References Cited

U.S. PATENT DOCUMENTS

| | | | |
|---|---|---|---|
| 1,109,103 | 9/1914 | Baum | 165/119 |
| 2,190,598 | 2/1940 | Fischer | 210/12 |
| 2,315,577 | 4/1943 | Bach | 210/12 |
| 3,139,067 | 6/1964 | VanDenBroek et al. | 165/163 |
| 3,388,057 | 6/1968 | Callahan | 48/197 A |
| 3,487,015 | 12/1969 | Boester | 210/12 |
| 4,134,830 | 1/1979 | Skogman et al. | 48/197 A |

FOREIGN PATENT DOCUMENTS

483823  8/1953  Italy .......................................... 165/163

OTHER PUBLICATIONS

Culp et al., Advanced Wastewater Treatment, "Selecting and Combining Unit Processes," pp. 271–285, Van Nostrand Reinhold Co.

Primary Examiner—S. Leon Bashore
Assistant Examiner—George C. Yeung
Attorney, Agent, or Firm—Wellington M. Manning, Jr.; Luke J. Wilburn, Jr.

[57] ABSTRACT

A process of treating an animal manure slurry susceptible to aerobic composting and anaerobic microbiological degradation with the production of a fuel gas, comprises: separating the slurry into a first, solids concentrated, fraction of relatively coarse particle size, and a second, solids dilute, fraction of relatively fine particle size; carrying out on the first fraction an aerobic composting reaction which is exothermic; carrying out on the second fraction an anaerobic microbiological reaction in which a fuel gas comprising methane is produced; and utilizing heat from the exothermic reaction to promote the fuel gas producing reaction. The plant for carrying out the process advantageously comprises a reactor for the exothermic reaction comprising a frusto-conical outer shell portion within which is located a heat exchanger of conical cage configuration; liquor from the anaerobic reaction circulates through the heat exchanger for heat exchange with solid composting material passing downwardly through the frusto-conical shell portion in direct contact with the heat exchanger.

14 Claims, 4 Drawing Figures

MICROBIOLOGICAL PROCESSES TO PRODUCE FUEL GAS

This invention is concerned with improvements in or relating to slurry treatment utilising microbiological reactions.

Microbiological reactions are widely used in industry. For example, the conventional process of solids composting involves an exothermic aerobic microbiological reaction; and one well known effluent disposal procedure involves an anaerobic microbiological digestion, with the production of methane.

It is well known, for example, that the disposal of organic effluent slurries at times presents a problem. For example, animal manure slurries produced in agriculture, if not effectively treated, can be an affront to the environment because of their particularly strong polluting characteristics. Anaerobic digestion with the production of methane is attractive in this context, having regard to the energy value of the methane produced, the deodorizing effect on the effluent, and improved performance as a fertiliser.

It is an object of the present invention to provide an improved process of treating a slurry, particularly but not exclusively, applicable to effluent treatment.

It is another object of the invention to provide improved microbiological treatment plant.

It is another object of the invention to provide an improved reactor for carrying out an exothermic microbiological reaction.

The invention provides a process of treating a slurry susceptible to microbiological degradation comprising the steps of (a) separating the slurry into a first, solids concentrated, fraction, and a second, solids dilute fraction; (b) carrying out on the first fraction an exothermic microbiological reaction; (c) carrying out on the second fraction, a second microbiological reaction; and (d) utilising heat from the exothermic reaction to promote the second microbiological reaction.

The invention also provides a process of treating an organic effluent slurry susceptible to aerobic composting and anaerobic microbiological degradation with the production of a fuel gas, comprising the steps of (a) separating the slurry into a first, solids concentrated, fraction of relatively coarse particle size, and a second, solids dilute, fraction of relatively fine particle size; (b) carrying out on the first fraction an aerobic composting reaction which is exothermic; (c) carrying out on the second fraction an anaerobic microbiological reaction in which a fuel gas comprising methane is produced in the presence of mesophilic microorganisms comprising methanogenic bacteria; and (d) utilising heat from the exothermic reaction to promote the fuel gas producing reaction.

The invention also provides fuel gas when produced by a process according to the invention.

The invention also provides a solid by-product of a process according to the invention.

The invention also provides slurry treatment plant adapted for use in carrying out a process according to the invention, and comprising (a) means for separating the slurry into a first, solids concentrated, fraction of relatively coarse particle size, and a second, solids dilute, fraction of relatively fine particle size; (b) a first aerobic, microbiological reactor; (c) a second, anaerobic, microbiological reactor; (d) heat exchange means for utilising heat from an exothermic microbiological reaction carried out in the first reactor to promote a fuel gas producing microbiological reaction in the second reactor; (e) means for conducting the first fraction from the separating means to the first reactor; and (f) means for conducting the second fraction from the separating means to the second reactor.

The invention also provides a reactor adapted for use in a process according to the invention and comprising (a) an outer shell which comprises a downwardly diverging frusto-conical portion; and (b) a heat exchanger of a downwardly diverging conical cage configuration located within the shell spaced from the frusto-conical shell portion; the heat exchanger being arranged for conduction of liquid therethrough for heat exchange with solid material passing downwardly through the frusto-conical shell portion in direct contact with the heat exchanger.

The invention also comprehends slurry treatment plant comprising such a reactor.

There now follows a description, to be read with reference to the accompanying drawings, of plant embodying the invention. This description, which is also illustrative of process and product aspects of the invention, is given by way of example only, and not by way of limitation of the invention.

Figure 1:
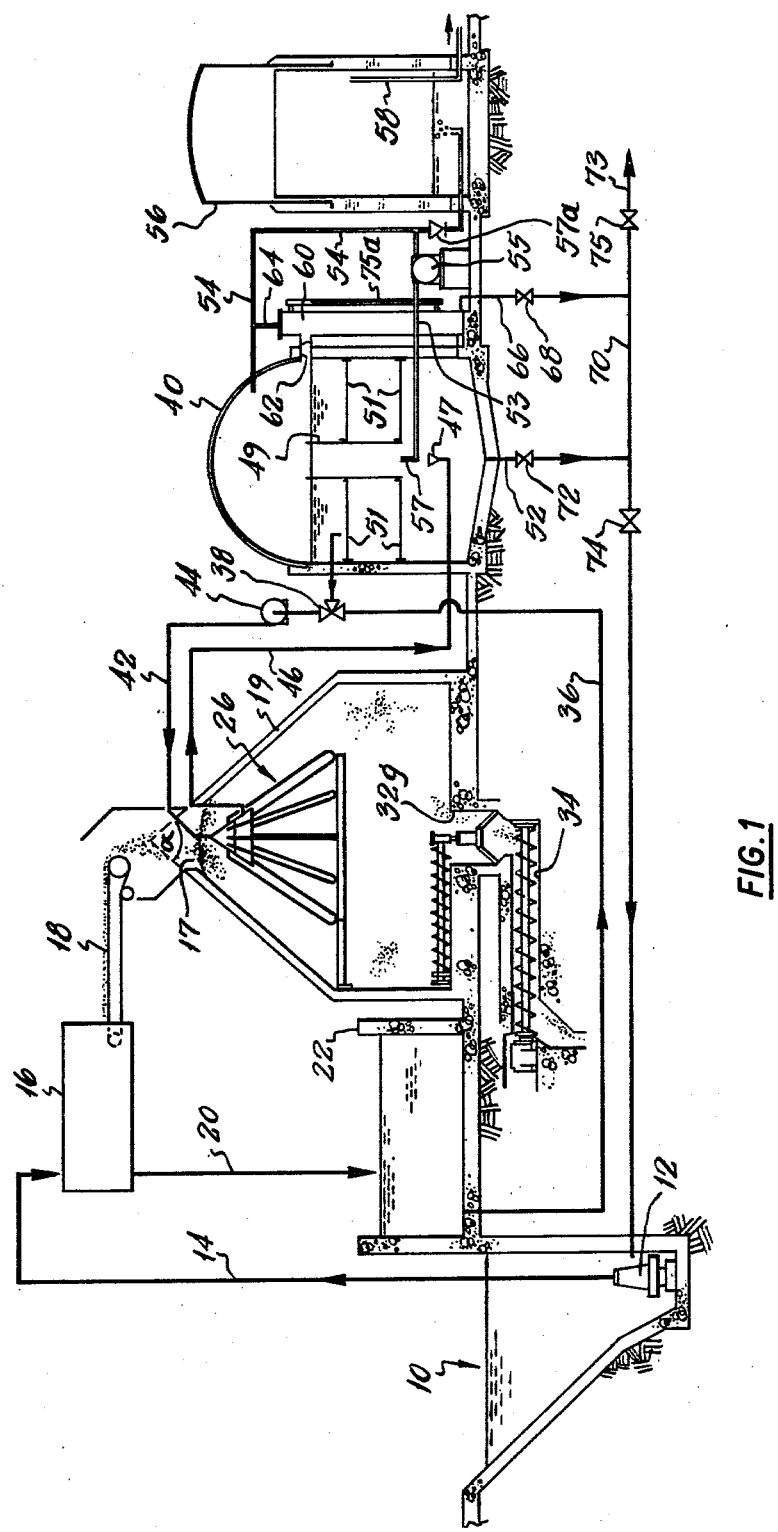
FIG. 1 shows a flow diagram of the plant embodying the invention.

The plant embodying the invention comprises a pit 10 for the reception of an agricultural fibrous organic effluent slurry, which is, for example, animal manure, such as pig, cattle or poultry manure. A submersible pump 12 is located in the pit 10, and a line 14 leads therefrom to a solid/liquid separator 16 which is substantially as described in my U.K. patent specification No. 1,437,336, the entire disclosure of which is incorporated herein by reference; the separator 16 as described therein comprises an endless belt screen with pressure rollers. In the operation of the plant, the separator 16 separates the slurry into a first, solids concentrated, fraction of a relatively coarse particle size, and a second, solids dilute, fraction of a relatively fine particle size. The first fraction is generally solid in consistency having a sawdust-like or peaty feel, and the second fraction generally liquid in consistency. A line 20 leads from the separator 16 to a holding tank 22 for the second fraction, and a belt conveyor 18 is arranged to convey the first fraction from the separator 16 to an inlet 17 of a first, aerobic composting, reactor 19, in which in the operation of the plant the first fraction is subject to a spontaneous aerobic exothermic composting reaction.

Figure 2:
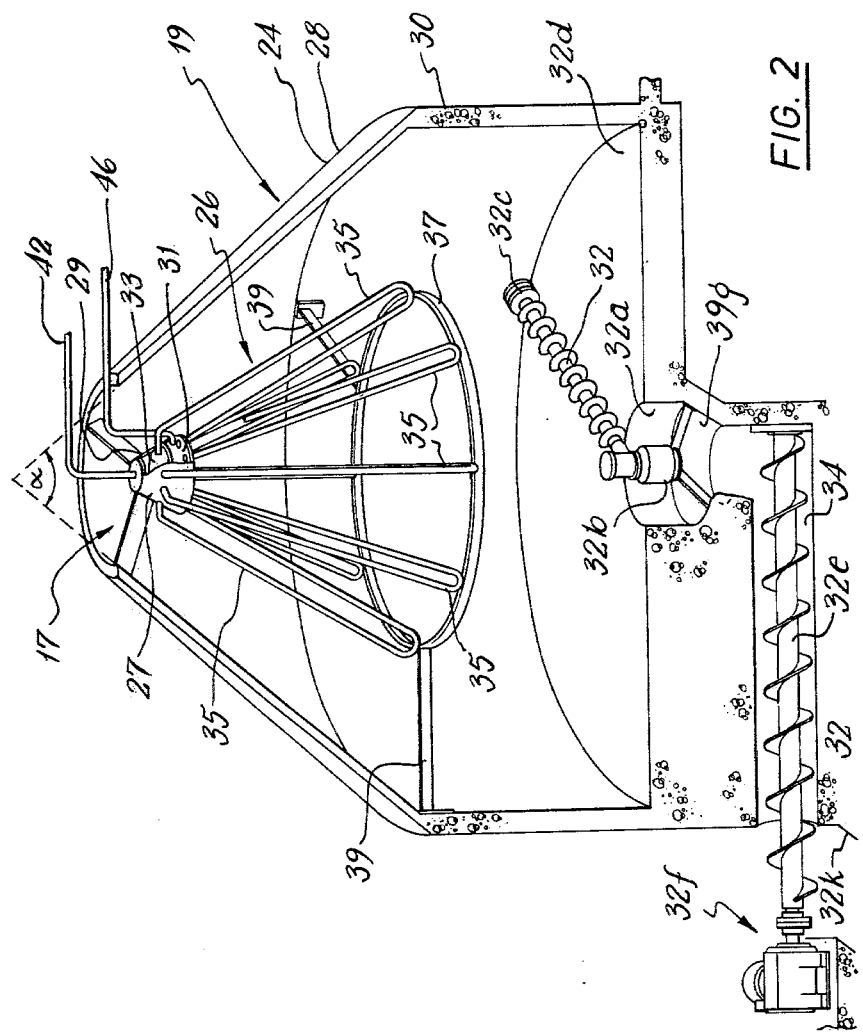
FIG. 2 shows a pictorial view of a composting reactor of the plant.

The reactor 19 (FIG. 2) comprises a thermally insulated (for convenience lagging is not shown) outer shell 24, comprising a downwardly diverging frusto-conical upper portion 28 and a circular cylindrical lower portion 30; the inlet 17 is located at the upper extremity of the frusto-conical portion 28. A heat exchanger 26 of downwardly diverging conical cage configuration is centrally located within the frusto-conical upper portion 28 of the shell 24, the heat exchanger being spaced from the shell portion 28.

The heat exchanger 26 comprises a frusto-conical manifold 27 which is divided into flow and return portions 29, 31 respectively by a horizontal plate 33. the heat exchanger also comprises a plurality of evenly spaced similar pipe loops 35 which define the generally conical configuration. Each pipe loop 35 communicates with the flow and return portions of the manifold 27. Lower end portions of the loops 35 are joined by a solid ring 37. The heat exchanger 26 is supported in the shell portion 28 by struts 37 extending from the manifold 27 to the shell 24, and by struts 39 extending from the ring 37 to the shell 24. Pipe lines 42, 46 lead respectively to the flow and return manifold portions 29, 31.

A discharge auger 32 is located in the cylindrical lower portion 30 of the shell 24. The discharge auger 32 is arranged not only for rotation about its own axis but also to traverse the lower shell portion 30 about the vertical axis of the reactor 19. The auger 32 is pivoted for its traversing movement in a well 32a and is rotated about its own axis by a motor and gearbox 32b located in the well 32a. Wheels 32c are mounted on an outer end portion of the auger 32 and rotate with the axial rotation of the auger 32. The wheels 32c engage a horizontal floor portion 32d of the reactor 19 and as they rotate cause the traversing movement of the auger 32. A discharge conduit 34 leads from the well 32a horizontally out of the reactor 19, and another auger 32e is located within the discharge conduit 32; the auger 32e is driven by a motor and gearbox 32f. A chute 32g in the well 32a leads from the auger 32 past the motor and gearbox 32b towards the auger 32e. The auger 32e is arranged to discharge via a chute 32k, which leads, for example, to an elevator conveyor (not shown).

In the operation of the plant, the first fraction is composted as it passes downwardly from the inlet 17 through the reactor 19; the composted solids are withdrawn at 34 by intermittent operation of the augers 32, 32e, which may be thermostatically controlled according to temperature conditions in the reactor 19; and heat from the exothermic composting reaction is yielded up to the heat exchanger 26 by the solid composting material as it passes downwardly through the reactor 19 in direct contact with the loops 35 of the heat exchanger 26. Provision may be made for recycling a portion of the composted solids discharged at 32k to the inlet 17 if required for operational reasons. Intermittent operation of the separator 16 and the conveyor 18 feeds fresh material to the reactor 19. Also, operation of the auger 32 loosens the contents of the reactor 19, and thereby, facilitates distribution of atmospheric air which enters via 34 for the aerobic reaction. If desired, special ventilation louvres (not shown) may be provided for additional access of atmospheric air. Again, oxygen enriched air may be supplied by a pump. There is the further possibility of inducing air flow through the reactor 19 by a downstream fan, which air could then be discharged to atmosphere from the fan or recirculated through the reactor 19.

The conical angle $\alpha$ of the frusto-conical shell portion 28 is chosen so that the slope of the shell portion 28 corresponds to the natural angle of repose of the material passing into the reactor 19 through the inlet 17; the angle $\alpha$ is, for example, between 80° and 100°, e.g. about 90°. The corresponding conical angle of the heat exchanger 26 is less than that of the shell portion 28, and is, for example, between 50° and 70°, e.g. about 60°.

A line 36 leads from the holding tank 22 via a valve 38 to a second, anaerobic, reactor 40, in which the second fraction is subjected to an anaerobic digestion reaction with the production of a fuel gas comprising methane; this reaction is effected by mesophilic methanogenic microorganisms comprising methanogenic bacteria; in a modification thermophilic microorganisms are employed. The line 42 leads from the valve 38 via a circulating pump 44 to the heat exchanger 26, and the return line 46 leads from the heat exchanger 26 back to the reactor 40, the line 46 terminating in a distributor 47. In the operation of the plant, material is circulated by the pump 44 through the line 42 to the heat exchanger 26 where the material is heated, and then back to the reactor 40 along the line 46. Thus, it will be realised that heat generated by the exothermic reaction in the reactor 19 is utilised to promote the anaerobic reaction in the reactor 40.

Figure 3:
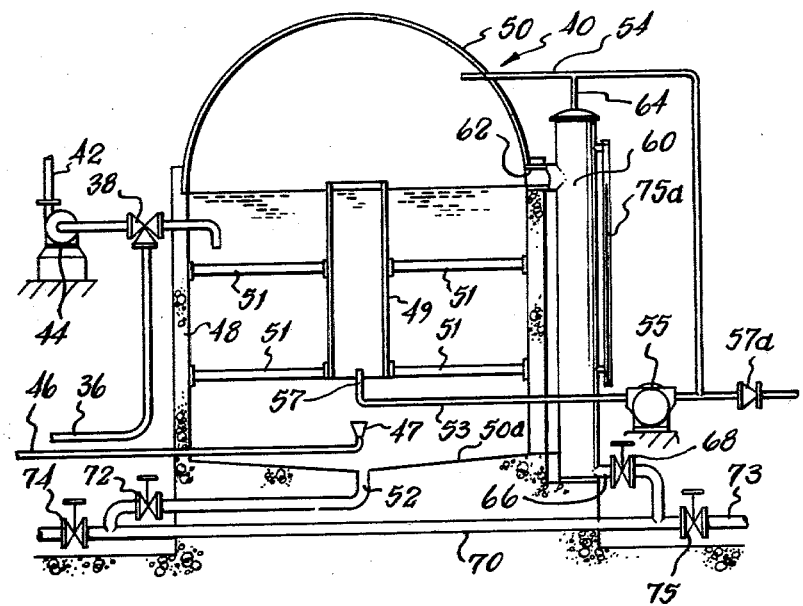
FIG. 3 shows a sectional side view of an anaerobic reactor of the plant.

The reactor 40 (FIG. 3) comprises a thermally insulated (again for convenience lagging is not shown) circular cylindrical lower shell portion 48 and an upper domed portion 50 which may be rigid or flexible and/or expansible. In the operation of the plant, the fuel gas collects in the domed portion 50 above the level of liquor in the reactor 40. An inverted frusto-conical lower portion 50a of the reactor 40 is provided with lower exit means 52 for the periodic withdrawal of sludge produced in the anaerobic digestion, and grit. A line 54 leads from the domed portion 50 to a gas holder 56, in which the fuel gas is collected over water; the line 54 terminating below the water level. A utility gas line 58 leads from the gas holder 56 above the level of the water therein.

A vertical draught tube 49 is supported within the reactor 40 by struts 51 and extends for a short distance above the distributor 47 to just above the level of the liquor in the reactor 40. A gas line 53 leads via a gas pump 55 from the line 54 to an outlet 57 at the lower end of the draught tube 49; in the operation of the reactor injection of fuel gas at 57 promotes circulation of the material in the reactor 40 upwardly through the draught tube 49 and downwardly outside the draught tube 49. A non-return valve 57a is provided in the line 54 to guard against the risk of the fan 55 sucking water from the gas holder 56 in the event of a gas pressure drop. The valve 38 is a two-way valve and the level of liquor in the reactor 40 is maintained by operating the two-way valve 38 so that material from the tank 22 passes along the line 36 via the valve 38, the line 42, the heat exchanger 26 and the line 46 to the reactor 40 to replace material withdrawn from the reactor in a manner to be explained; at this time there is no flow direct from the reactor 40 through the valve 38. When sufficient material has been supplied from the tank 22, the two-way valve 38 is changed over to restore circulation direct from the reactor 40 through the heat exchanger 26 and back to the reactor 40. The valve 38 may be motorised and changed over at regular intervals by a timing device (not shown).

An upright overflow vessel 60 is located alongside the reactor 40 and communicates with the reactor 40 by an overflow pipe 62. Pressure in the vessel 60 is equalised by connection to the line 54 via a line 64. The vessel 60 is provided with sludge exit means 66 which leads via a valve 68 into a line 70. The exit means 52 from the reactor 40 also leads into the line 70 via a valve 72. The line 70 leads via a valve 74 into the pit 10 and also comprises a branch 73 leading to a sludge pit (not shown); the branch 73 includes a valve 75.

In the operation of the plant, as fresh material from the line 36 enters the reactor 40, material overflows into the vessel 60 and digested sludge settles towards the bottom of the vessel 60. A sight glass 75a is provided to indicate filling of the vessel 60. Material is withdrawn via the exit means 66 and valve 68 intermittently as necessary. If the material is simply for disposal, valves 68 and 75 are open and the material passes via the branch 73 to the sludge pit, from where it may be removed as required. At this time the valves 72, 74 are closed. It is only occasionally necessary to open the valve 72 to remove solid material from the portion 50a of the reactor 40. At times it is desirable to recirculate sludge from the exit means 66 to maintain the population of methanogenic microorganisms. In this case the valve 75 is closed and the valves 68, 74 are open; the sludge passes by the line 70 to the pit 10.

Figure 4:
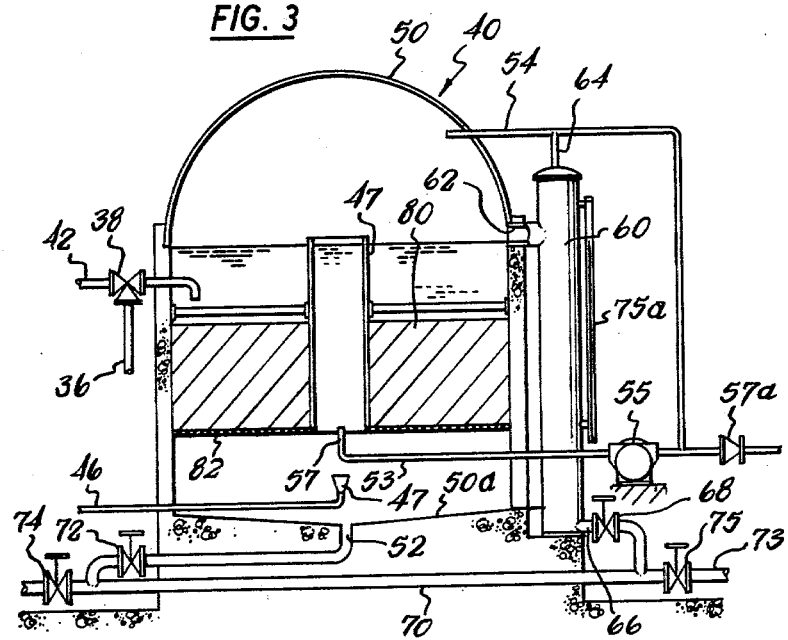
FIG. 4 shows a sectional side view of a modified anaerobic reactor.

In a modification (FIG. 4), the draught tube 47 is surrounded by submerged biological filter material 80 supported on a grid 82; the material 80 is a plastic material e.g. pvc, which provides an extended surface area to promote gas production. The filter material is particularly useful when the material in the reactor 40 has a relatively low suspended solids content.

In a further modification, the heat supply to the reactor 40 is supplemented by combustion of some of the fuel gas.

An additive rich in soluble carbohydrate may be added to the material in the reactor 40; this enhances the C:N ratio of the material involved in the fuel gas producing reaction in the reactor 40 and promotes the anaerobic reaction. An optimum C:N ratio (weight/weight) is, for example, between 15:1 and 30:1, e.g. between 25:1 and 30:1. One example of such an additive material is slurry from a potato peeling process. Also, it may be advantageous to utilise a phosphate additive.

The dry matter content of the slurry in the pit 10 is between 5 and 15% by weight, e.g. between 10 and 12%; the first fraction leaving the separator 16 and which is involved in the exothermic reaction, has a dry matter content of at least 20% by weight, e.g. between 25% and 30%; and the material in the reactor 40 has a dry matter content not greater than 8%, e.g. between 3% and 7% by weight in the absence of the biological filter material; and if the filter material is used, the dry matter content may be as low as 0.3%.

The exothermic reaction in the reactor 19 takes place at a temperature between 40° C. and 65° C., or up to 70° C. with oxygen enrichment, and the fuel gas producing reaction in the reactor 40 employing mesophilic microorganisms takes place at a temperature between 30° C. and 45° C., e.g. about 35° C. If thermophilic microorganisms are employed the temperature range is higher, from 55° C. to 70° C.

The residence time of the material in the reactor 19 is at least 5 days, and the residence time of the material in the reactor 40 is between 5 and 20 days. When mesophilic microorganisms are employed, e.g. about 10 days. If thermophilic microorganisms are used the residence time in the reactor 40 may be between 3 and 20 days.

The particle size of the composting material in the reactor 19 is between 1 mm. and 25 mm.

The particle size of suspended solid material in the reactor 40 is not greater than 1 mm. and for example 90% of the solid material has a particle size not greater than 200 microns.

The pH of the material in the reactor 40 is near neutral, between 6.8 and 8, e.g. about 7.5.

Separation of the initial slurry from the pit 10 into two fractions facilitates the provision of optimum conditions for the anaerobic reaction and also for the composting reaction. For example, the separation readily enables the particle size of the material in the reactor 40 to be adjusted to the optimum range for the anaerobic digestion and also adjustment of the dry matter content to the optimum range with either no addition of water or only minimum addition of water to reduce ammonia concentration if necessary to avoid inhibition of the microbiological reaction; this is rarely necessary with agricultura slurries. Again, the material entering the reactor 40 has a higher proportion of soluble BOD than the original material in the pit 10, and this accelerates the microbiological reaction in the reactor 40. It will be understood that the characteristics of the two fractions are readily variable by changing the screen of the separator for one of different screening characteristics.

If the initial slurry were subjected to anaerobic digestion without the solid-liquid separation, the coarser solids would still contribute to the energy requirements of the anaerobic reaction, but I believe the separate composting step may increase the heat energy contribution by a factor of the order of ten-fold.

In addition to the value of the fuel gas produced, solid by-products of value are produced: viz, the composted solids can be used as an enriched garden fertiliser, and the material from the reactor 40 is a reasonably environmentally acceptable agricultural fertiliser, which may be used separately or mixed with the composted solids. Generally, control of pathogens is facilitated.

The loading rate of the reactor 40 is for example, between 0.96 and 6.4 Kgs. volatile solids/cu. meter/day, e.g. about 4.7 Kgs/cu. meter at 7% suspended solids. Methane gas is produced for example, at a rate of between 0.1 and 0.4 cubic meters/Kg. volatile solids, e.g. about 0.2 cubic meters/Kg. volatile solids.

The concentration of ammoniacal nitrogen in the reactor 40 is, for example, not greater than 3000 mg/liter N.

The fuel gas produced comprises 60–70% by volume methane, and a typical overall composition by volume is as follows:

$CH_4$: 60–70%
$H_2$: 1–3%
$O_2$: 0.5–1%
$CO_2$: 30–35%
Miscellaneous gases: 1–3%

EXAMPLE 10,000 lbs. per day of pig manure slurry derived from the activities of 1000 pigs had a total dry matter content of 8% by weight. This was separated in a separator 16 having a screen of 800 micron mesh apertures into a concentrated fraction of 1000 lbs. per day at a total dry matter content of 25% by weight and a dilute fraction of 9,000 lbs. per day at 6% total dry matter content. A temperature of 65° C. was achieved in composting the first fraction.

The concentrated fraction when composted yields 750,000 BTU per day of heat energy, which should be sufficient to maintain the anaerobic reaction in the second fraction in the reactor 40 at a reasonable rate even on cold days without using any of the fuel gas for this purpose.

By way of comparison, in a conventional anaerobic digester used under U.K. weather conditions, up to 40% of the fuel gas produced through the year is used in maintaining the necessary temperatures in the reactor.

I claim:

1. A process of treating an organic effluent slurry susceptible to aerobic composting and anaerobic microbiological degradation with the production of a fuel gas, comprising the steps of (a) separating the slurry into a first, solids concentrated, fraction of relatively coarse particle size, and a second, solids dilute, fraction of relatively fine particle size; (b) carrying out on the first fraction an aerobic composting reaction which is exothermic; (c) carrying out on the second fraction an anaerobic microbiological reaction in which a fuel gas comprising methane is produced in the presence of microorganisms comprising methanogenic bacteria; and (d) utilising heat from the exothermic reaction to promote the fuel gas producing reaction.

2. A process according to claim 1, wherein the slurry is an agricultural fibrous organic slurry.

3. A process according to claim 1, wherein the slurry is an animal manure slurry.

4. A process according to claim 1, wherein the slurry has a dry matter content between about 5 and about 15% by weight.

5. A process according to claim 1, wherein the fraction involved in the fuel gas producing reaction has a dry matter content not greater than about 8% by weight.

6. A process according to claim 1, wherein the fuel gas producing reaction is promoted by use of an extended surface area provided by a biological filter material.

7. A process according to claim 6, wherein the fraction involved in the fuel gas producing reaction has a dry matter content not less than about 0.3%.

8. A process according to claim 1, wherein the particle size of the fraction involved in the fuel gas producing reaction is not greater than about 1 mm.

9. A process according to claim 1, wherein the particle size of the fraction involved in the exothermic reaction is between about 1 mm. and about 25 mm.

10. A process according to claim 1, wherein the fraction involved in the exothermic reaction has a dry matter content of at least about 20% by weight.

11. A process according to claim 1, wherein the exothermic reaction takes place at a temperature between about 40° C. and about 70° C., and the fuel gas producing reaction takes place at a temperature between about 30° C. and about 45° C.

12. A process according to claim 1, wherein the exothermic reaction is carried out in a first reactor; the fuel gas producing reaction is carried out in a second reactor; and fraction involved in the fuel gas producing reaction is heated by circulation through a heat exchanger which is in direct contact with fraction involved in the exothermic reaction.

13. A process according to claim 1 wherein the micro-organisms are mesophilic.

14. A process according to claim 1 wherein the micro-organisms are thermophilic.

* * * * *